United States Patent
Sato et al.

(10) Patent No.: US 6,508,766 B2
(45) Date of Patent: Jan. 21, 2003

(54) ULTRASOUND DIAGNOSTIC APPARATUS

(75) Inventors: Takeshi Sato, Nasu-gun (JP);
Masamichi Oyanagi, Otawara (JP);
Yoshitaka Mine, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 118 days.

(21) Appl. No.: 09/754,129

(22) Filed: Jan. 5, 2001

(65) Prior Publication Data

US 2001/0009977 A1 Jul. 26, 2001

(30) Foreign Application Priority Data

Jan. 20, 2000 (JP) .......................... 2000-012108

(51) Int. Cl.[7] ................................ A61B 8/00
(52) U.S. Cl. ...................................... 600/441
(58) Field of Search ................. 600/440, 441, 600/443, 447, 437, 442, 449

(56) References Cited

U.S. PATENT DOCUMENTS

| | | | | |
|---|---|---|---|---|
| 5,855,556 A | * | 1/1999 | Shirai | 600/440 |
| 5,879,302 A | * | 3/1999 | Hashimoto et al. | 600/441 |
| 5,980,459 A | | 11/1999 | Chiao et al. | |
| 6,074,348 A | | 6/2000 | Chiao et al. | |
| 6,186,949 B1 | * | 2/2001 | Hatfiled et al. | 600/443 |

FOREIGN PATENT DOCUMENTS

| | | |
|---|---|---|
| JP | 8-280674 | 10/1996 |
| JP | 11-318902 | 11/1999 |

OTHER PUBLICATIONS

D. H. Simpson, et al., IEEE Transactions on Ultrasonics, Ferroelectrics, and Frequency Control, vol. 46, No. 2, pp. 372–382, "Pulse Inversion Doppler: A New Method for detecting Nonlinear Echoes From Microbubble Contrast Agents", Mar. 1999.

* cited by examiner

Primary Examiner—Francis J. Jaworski
Assistant Examiner—Maulin Patel
(74) Attorney, Agent, or Firm—Oblon, Spivak, McClelland, Maier & Neustadt, P.C.

(57) ABSTRACT

An ultrasound diagnosis apparatus includes an ultrasound probe and a beam-former configured to scan an object to be examined with ultrasound waves through the ultrasound probe. A B-mode processor generates B-mode image data on the basis of a reception signal output from the beam-former. A power Doppler processor generates power Doppler data on the basis of the reception signal output from the beam-former. The power Doppler data is generated on the basis of the reception signal acquired under transmission conditions that the burst wave number is equal or substantially equal to that for the B-mode data, and the ensemble size is set to one of 2 to 10. The B-mode image data and power Doppler data are partly synthesized.

19 Claims, 5 Drawing Sheets

ULTRASOUND DIAGNOSTIC APPARATUS

CROSS-REFERENCE TO RELATED APPLICATIONS

This application is based upon and claims the benefit of priority from the prior Japanese Patent Application No. 2000-012108, filed Jan. 20, 2000, the entire contents of which are incorporated herein by reference.

BACKGROUND OF THE INVENTION

The present invention relates to a color Doppler ultrasound diagnosis apparatus and, more particularly, to an improvement in the performance of a power Doppler image for displaying power from a bloodstream.

As a method of two-dimensionally displaying a bloodstream, a color Doppler method is available. In the color Doppler method, a Doppler shift (frequency shift) caused by the flow of blood is extracted, and three types of bloodstream information, i.e., an average flow rate, dispersion, and power, are generated from the Doppler shift. A two-dimensional image associated with this bloodstream information is displayed in color. Typically, this color image is superimposed on a monochrome tomographic image (B-mode image).

Note that a method of displaying the power information of a bloodstream is called a power Doppler method, and a method of displaying the flow rate and/or dispersion information of the bloodstream is called a color Doppler method; these two methods are discriminated from each other.

Power Doppler is superior in sensitivity and resolution over color Doppler, and hence tends to be preferentially used as a method of displaying a region other than the heart.

In power Doppler (as well as in color Doppler), the frame rate (time resolution) is much lower than in B-mode. In addition, power Doppler is inferior in distance resolution to B-mode.

There are several reasons why power Doppler is inferior in distance resolution to B-mode. The main reason is that a long wave train length is set.

The main reason why color Doppler and power Doppler are inferior in time resolution to B-mode is that ultrasound pulses are repeatedly transmitted/received in the same direction in color Doppler and power Doppler. Transmission/reception is repeated 8 to 20 times generally, and 16 times typically. The number of times of this operation is termed as an ensemble size. If this ensemble size is small, clutter cannot be completely removed by a wall filter. For this reason, the ensemble size cannot be set to be very small. Therefore, an improvement in time resolution cannot be expected.

Recently, a great deal of attention has been paid to a contrast echo method which performs ultrasound diagnosis by injecting an ultrasound contrast medium mainly consisting of microbubbles intravenously. Visualizing methods for this method are roughly classified into three methods, namely a harmonics B-mode method, a general power Doppler method using fundamental waves, and a harmonics power Doppler method. Of these three methods, the power Doppler method using fundamental waves exhibits the highest bloodstream sensitivity. In the contrast echo method, an intra-tissue bloodstream, i.e., perfusion, is often observed. In the power Doppler method, therefore, problems often arise in terms of clutter.

In the harmonics power Doppler method, no clutter occurs. However, this method is inferior in resolution to harmonics B-mode, and exhibits no significant difference in sensitivity. For this reason, harmonics B-mode is generally used in many cases. In the contrast echo method, since echoes are enhanced by a contrast medium injected into a blood vessel, a bloodstream can be observed in B-mode.

In the contrast echo method, perfusion can be effectively visualized by setting a high MI (Mechanical Index) value representing the power of ultrasound waves in an object. In general, reflected echoes from an intra-tissue bloodstream are small. However, strong reflected echoes can be generated by destroying microbubbles by transmitting ultrasound waves with a high MI value. On the other hand, since ultrasound waves with a high MI value destroy most microbubbles, next ultrasound transmission must be performed after fresh microbubbles are injected. For this purpose, a so-called flash echo method has been developed, which intermittently repeats ultrasound transmission with a high MI value. This flash echo method is disclosed in Jpn. Pat. Appln. KOKAI Publication No. 8-280674. This flash echo method, however, exhibits a low time resolution.

In order to remove this demerit, a power pulse inversion method has been developed. In this method, ultrasound waves are transmitted with a low MI value so as not to destroy many bubbles. A decrease in sensitivity with a decrease in MI value is compensated for by removing clutter of fundamental waves and using both a fundamental wave and harmonics as bloodstream signals. That is, in this method, since a bloodstream is visualized by using both harmonics and fundamental wave, the sensitivity is higher than that in the conventional harmonics Doppler method. In addition, since the bloodstream drawing sensitivity in the power Doppler method is higher than that in B-mode, perfusion can be observed by continuously transmitting bubbles without destroying bubbles with a low MI value. However, the resolution is lower than that in bloodstream display in B-mode.

In the contrast echo method, to improve the distance resolution, attempts have been made to set the burst wave number in power Doppler to 1 to 2 as in B-mode. However, in this method the distance resolution is lower than that in B-mode.

The method of directly imaging a bloodstream in B-mode is disclosed in Jpn. Pat. Appln. KOKAI Publication No. 11-318902. In this method, a tissue image and bloodstream image are simultaneously displayed by partly filtering some of components in a B-mode band (near DC). In this method, since a tissue image and bloodstream image are completely generated from the same pulses, it is difficult to satisfy both requirements for the resolution of a tissue image (high-frequency, broadband pulses are effective) and penetration of a bloodstream image (low-frequency, narrowband pulses are effective).

BRIEF SUMMARY OF THE INVENTION

It is an object of the present invention to improve the distance resolution, sensitivity, and clutter removing effect and increase the frame rate in power Doppler.

An ultrasound diagnosis apparatus includes an ultrasound probe and a beam-former configured to scan an object to be examined with ultrasound waves through the ultrasound probe. A B-mode processor generates B-mode image data on the basis of a reception signal output from the beam-former. A power Doppler processor generates power Doppler data on the basis of the reception signal output from the beam-former. The power Doppler data is generated on the basis of the reception signal acquired under transmission conditions that the burst wave number is equal or substantially equal to that for the B-mode data, and the ensemble size is set to one of 2 to 10. The B-mode image data and power Doppler data are partly synthesized.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An apparatus according to a preferred embodiment of the present invention will be described below with reference to the views of the accompanying drawing.

The characteristic features of the present invention will be briefly described below. The present invention is characterized by performing the following processes.

(1) In the power Doppler mode, transmission pulses based on a 1 or 2 wave driving mode is used. Preferably, transmission pulses based on the 2 wave driving mode are used as in B-mode. In other words, in the power Doppler mode, broadband transmission pulses with a short wave train length are used as in B-mode.

(2) The ensemble size in the power Doppler mode is selected from 2 to 10, and more preferably, from 2 to 6. Most preferably, the ensemble size is set to 4. In a Doppler mode, ultrasound pulses need to be repeatedly transmitted in the same direction. The number of times of this repetitive transmission is termed as an ensemble size. The ensemble size in the color Doppler mode is 8 to 20, typically 16.

(3) No transmission exclusive to B-mode is performed, and reception signals acquired in the power Doppler mode are shared for power Doppler processing and B-mode processing.

(4) Averaging is performed by using beams transmitted in the same direction for power Doppler processing to generate a beam for B-mode.

(5) When a scanned/converted B-mode image and power Doppler image generated from the same reception signal are to be partly synthesized or composited into a 1-frame image, the pixel value of each pixel of B-mode image is compared with that of a corresponding pixel value of the power Doppler image, and a higher value is selected.

A supplemental explanation will be given below with regard to the above five characteristic features.

(1') By using a transmission pulse based on the 1 or 2 wave driving mode as in B-mode as a power Doppler transmission pulse, a power Doppler image can have substantially the same information as that of a B-mode image. If, for example, a wall filter is set to the through mode, the power Doppler image becomes almost identical to B-mode image. This phenomenon is closely related to an image synthesizing method.

(2') The ensemble size in a Doppler mode is generally set to 8 to 20. If the ensemble size is small, clutter cannot be sufficiently removed. In the present invention, however, this ensemble size is set to a very small value, e.g., 4. Although many clutter components remain, this clutter is information originating from the movement of a tissue, i.e., tissue information almost equivalent to that in B-mode. By partly synthesizing a power Doppler image and B-mode image, the tissue form between a power Doppler image portion and a B-mode image portion becomes continuous. In addition, reducing the ensemble size will improve the time resolution (frame rate).

(3') When the same transmission conditions can be set for the power Doppler mode and B-mode, ultrasound pulses for B-mode and power Doppler mode need not be transmitted separately, and transmission of ultrasound pulses can be shared in the two modes.

(4') When the same transmission conditions can be set for the power Doppler mode and B-mode, a B-mode image can be generated by using all beams in the same direction instead of using only one beam. When the ensemble size is 4, the number of beams in each direction is 4. By adding these four signals before detection, the S/N ratio can be increased. In addition, by detecting four signals through different reception filter characteristics and adding them, speckle noise can be removed.

Figure 1:
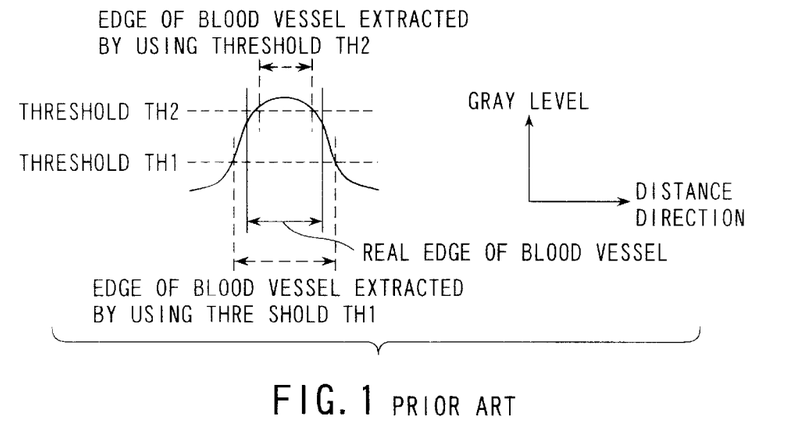
FIG. 1 is a view showing a problem raised when images are synthesized by using a threshold technique in the prior art.

(5') Consider the reason why a high distance resolution cannot be obtained when a 1-wave driving mode is set as a driving condition in the contrast echo method described in associated with the problems in the prior art as in B-mode. Obviously, a filter in the distance direction is set in the same condition as that in B-mode. A relatively high bloodstream sensitivity is ensured in the contrast echo method. The reason why a high distance resolution cannot be obtained lies in a method of synthesizing a power Doppler image and B-mode image. According to a conventional method of synthesizing a power Doppler image and B-mode image, the pixel values of the power Doppler image and B-mode image are selected in units of pixels, and each pixel is displayed by using a unique color map. According to a selection algorithm, when a given pixel value of the power Doppler image is equal to or larger than a predetermined threshold, this pixel value of the power Doppler image is selected for the corresponding pixel. On the other hand, when a given pixel value of the power Doppler image is less than the predetermined threshold, a corresponding pixel value of B-mode image is used for the pixel. For this reason, the thickness of a bloodstream is determined depending on the set threshold. More specifically, as shown in FIG. 1, when the threshold is set to an excessively low value, the expressed bloodstream becomes thicker than the actual one, and the resolution looks low. In contrast to this, when the threshold is set to an excessively large value, the expressed bloodstream becomes thinner than the actual one, and the sensitivity looks low. In the contrast echo method, since sufficiently high sensitivity is ensured, the threshold becomes relatively small, and the bloodstream tends to be expressed as a one thicker than the actual bloodstream. The resolution in this mode looks lower than that of a B-mode image. When a power Doppler image is singly displayed without any threshold processing, a B-mode tissue image is difficult to discern. In addition, when a power Doppler image is superimposed as a transmitted image on a B-mode image, a fine bloodstream is hidden behind B-mode image and cannot be seen.

In the present invention, as described above, the pixel value of each pixel of a B-mode image is compared with that of a corresponding pixel value of a power Doppler image, and a higher value is selected, thereby partly synthesizing B-mode image and power Doppler image. In this synthesized image, the power Doppler image portion is smoothly joined to B-mode image portion. This is a decisive difference between the synthesizing method of the present invention and the conventional synthesizing method. To connect such portions more smoothly, gray scale for B-mode display may be preferably used. Since a power Doppler image and B-mode image are partly synthesized in this manner without using any threshold, a deterioration in resolution can be theoretically prevented. In addition, although clutter remains in a power Doppler image portion because of a reduction in ensemble size, this clutter is smoothly joined to a tissue image of a B-mode image portion, and hence can be effectively used as a tissue image instead of an artifact that interferes with a bloodstream image. As described above, the clutter in the power Doppler image is essentially the same information as B-mode image. In a power Doppler image, clutter is recognized as noise (artifact). However, by synthesizing it with a B-mode image, the clutter can be used as significant information instead of noise. Assume that in a given pixel, the gray level of clutter in a power Doppler image is higher than that in B-mode, and the clutter is selected as the corresponding pixel. Even in this case, this pixel can be recognized as a tissue image. In the conventional color Doppler and power Doppler methods, the most significant challenge is to remove clutter, and various techniques have been tried. In the present invention, however, residual clutter itself raises no problem, and can be effectively used instead. In the conventional method, to sufficiently remove clutter with a filter, the cutoff frequency is set to be relatively high. For this reason, slow bloodstream components are removed, together with clutter. In the present invention, since there is no need to remove clutter, the sensitivity to slow bloodstream components improves.

Figure 2A:
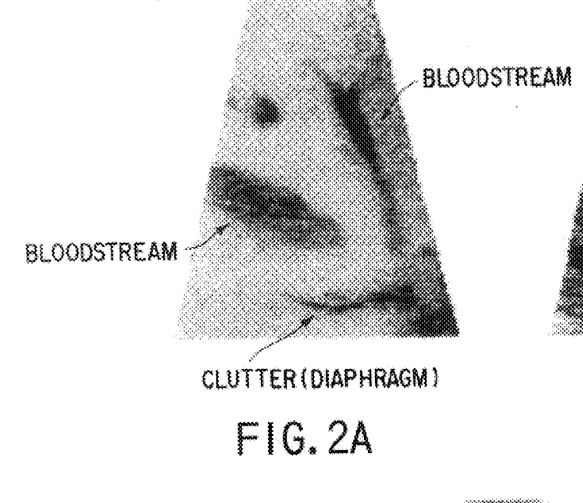
FIG. 2A is a view showing a power Doppler image sample displayed singly on a display in the present invention.
Figure 2B:
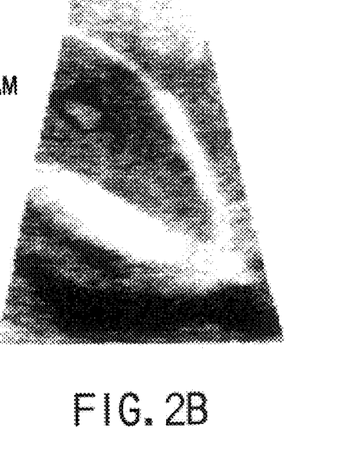
FIG. 2B is a view showing a B-mode image sample displayed singly on the display in the present invention.
Figure 2C:
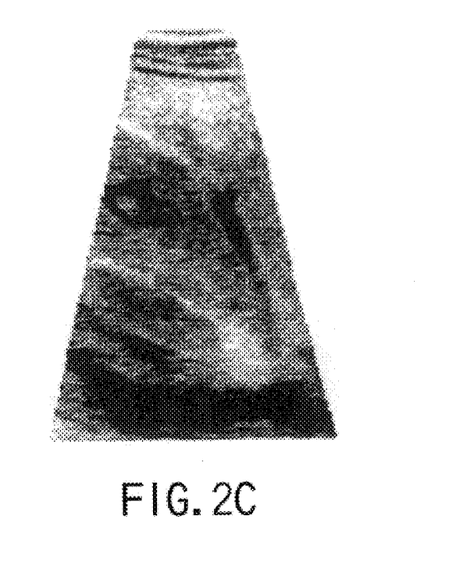
FIG. 2C is a view showing a synthetic or composite image sample generated from a power Doppler image and B-mode image and displayed on a display in the present invention.

FIGS. 2A, 2B, and 2C show actual image samples. FIGS. 2A, 2B, and 2C respectively show a power Doppler image, B-mode image, and synthetic image. The power Doppler image contains clutter (tissue image) together with a bloodstream image. In the synthetic image, this clutter is joined to a tissue image in a B-mode image portion and can be recognized as a tissue image instead of an artifact.

Note that when a tissue exhibits a very high luminance, a bloodstream may be hidden from view behind the high-luminance tissue. However, this method is essentially intended to be used for the contrast echo method, i.e., under the use of an ultrasound contrast medium. In this case, bloodstream echoes are strong, and a bloodstream is seen with flicker, i.e., time variations. For this reason, a bloodstream image can be easily discriminated from a tissue image. For this purpose, image processing in the frame direction (time-axis direction) such as persistence is not preferably performed.

Figure 3:
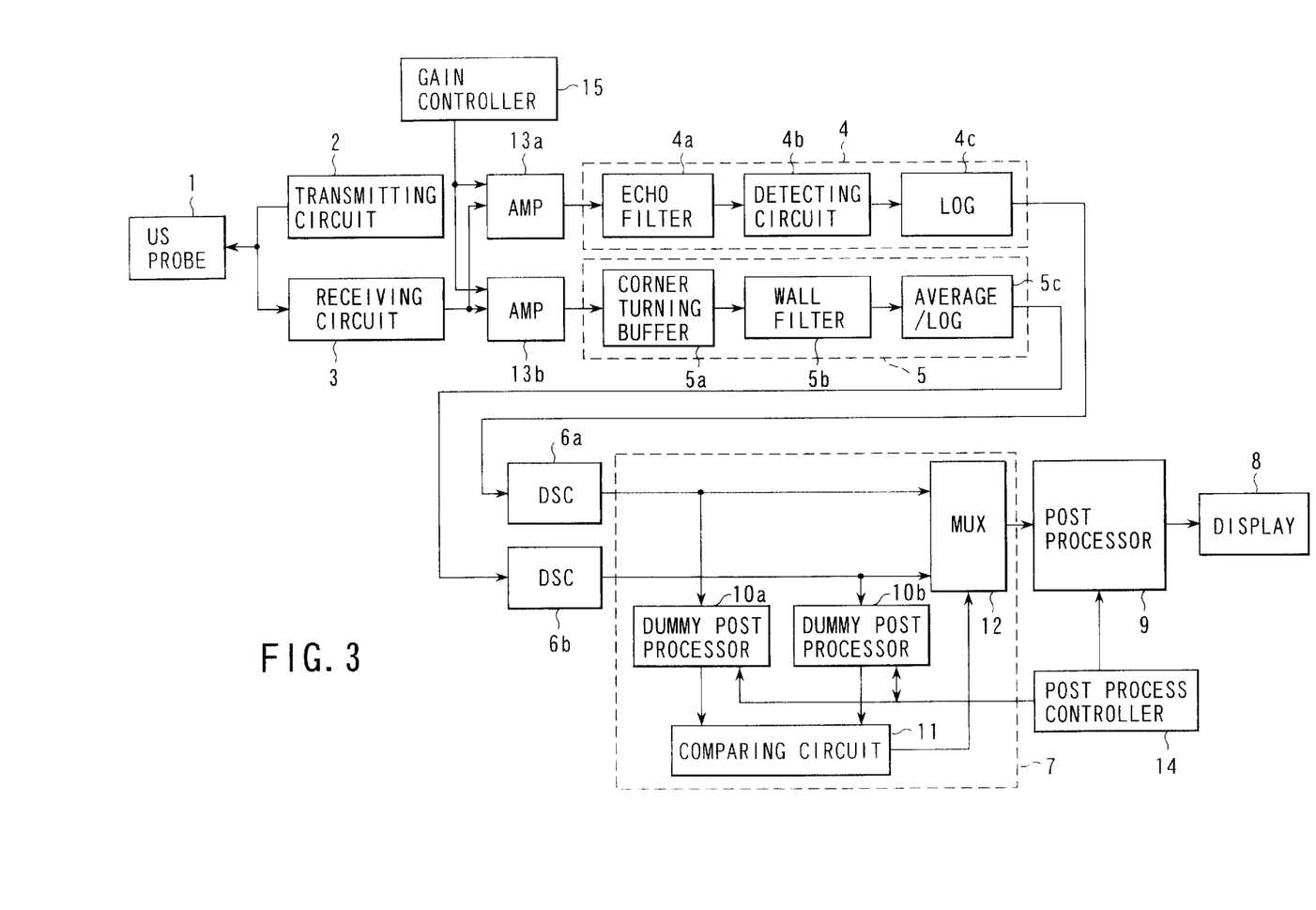
FIG. 3 is a block diagram showing the arrangement of an ultrasound diagnosis apparatus according to an embodiment of the present invention.

FIG. 3 is a block diagram showing an ultrasound diagnosis apparatus according to a preferred embodiment of the present invention. An ultrasound probe 1 has a plurality of vibrators arranged one- or two-dimensionally. A transmitting circuit 2 supplies a driving signal (high-frequency voltage pulse) to each vibrator. With this operation, ultrasound pulses are transmitted from the ultrasound probe 1. The transmitting circuit 2 generates driving signals in accordance with a predetermined pulse sequence (to be described later). With this operation, scan operation is performed in a predetermined pulse sequence. A receiving circuit 3 receives an echo signal returned from the object via the probe 1, and performs in-phase addition processing for the signal. The receiving circuit 3 then transforms the high-frequency signal into I and Q orthogonal signals. The I and Q signals are supplied to a B-mode processing unit 4 and power Doppler processing unit 5 via two amplifiers 13a and 13b. The amplifier 13a is set on the input stage of the B-mode processing unit 4. The amplifier 13b is set on the input stage of the power Doppler processing unit 5. By separately providing the amplifiers 13a and 13b for the processing units 4 and 5 in this manner, gains associated with B-mode processing and power Doppler processing can be separately set by a gain controller 15. The B-mode processing unit 4 has an echo filter 4a, detecting circuit 4b, and logarithmic compression circuit (LOG) 4c to generate a B-mode image. Methods of generating a B-mode image include a method of generating a B-mode image by using a fundamental wave component having the same frequency as that of a transmission pulse and a so-called harmonics method of generating a B-mode image by using a frequency component (secondary harmonic component) having a frequency twice that of a fundamental wave. In this embodiment, a B-mode image is generated by using the latter harmonics method.

A digital scan converter (DSC) 6a converts each ultrasound beam into orthogonal coordinates that can be displayed on a TV. The I and Q signals are also input to the power Doppler processing unit 5 and temporarily stored in a corner turning buffer 5a. Beams in the same direction are then extracted and sent to a wall filter 5b. The wall filter 5b has high-pass characteristics and serves to remove clutter from a still tissue and reduce clutter from a moving tissue. Note that the wall filter 5b uses a scheme of obtaining the average frequency of clutter and adaptively changing the filter coefficient depending on the obtained value.

An average/log 5c averages the power of an output signal string from the wall filter 5b and logarithmically compresses the resultant average signal. This output signal is converted into orthogonal coordinates by a digital scan converter 6b. An image synthesizing unit 7 partly synthesizes a B-mode image output from the DSC 6a of the B-mode system and a power Doppler image output from the DSC 6b of the power Doppler system. The resultant data is sent to a display 8 via a post processor 9 to be displayed as a gray-scale image. The post processor 9 converts an input signal into an RGB signal by using a lookup table. By selectively using lookup tables or switching parameters for a lookup table, various adjustments can be made, e.g., changing the display dynamic range by changing the input/output conversion characteristics, changing the display gain, emphasizing a specific gray level, and inverting a gray level.

The image synthesizing unit 7 has the function of comparing the pixel value of each pixel of a B-mode image with that of a corresponding pixel of a power Doppler image and selecting a higher value as that of the corresponding pixel. The image synthesizing unit 7 needs to compare the respective pixel values having undergone a post process. For this purpose, the image synthesizing unit 7 has dummy post processors 10a and 10b each performing the same processing as that performed by the post processor 9. One dummy post processor 10a performs a post process for the B-mode image, and the other dummy post processor 10b performs a post process for the power Doppler image. By providing two dummy post processors 10a and 10b in this manner, parallel processing can be performed in B-mode and power Doppler, thus ensuring real-time performance. Note that the conversion characteristics of the post processor 9 can be changed, as described above. Likewise, the conversion characteristics of the dummy post processors 10a and 10b can be changed. A post process controller 14 is provided to change the conversion characteristics of the dummy post processors 10a and 10b in accordance with the conversion characteristics of the post processor 9. With this arrangement, a comparing circuit 11 can compare the pixel value of each pixel of a B-mode image with that of a corresponding pixel of a power Doppler image in accordance with an actual display gray level. This comparison result is output to a multiplexer (MUX) 12. The multiplexer 12 selectively outputs the pixel values of the B-mode image and power Doppler image in units of pixels in accordance with the comparison result from the comparing circuit 11. The sections 9, 10a, 10b, 11, 12 and 14 can be implemented as a RAM or a ROM.

Figure 4A:
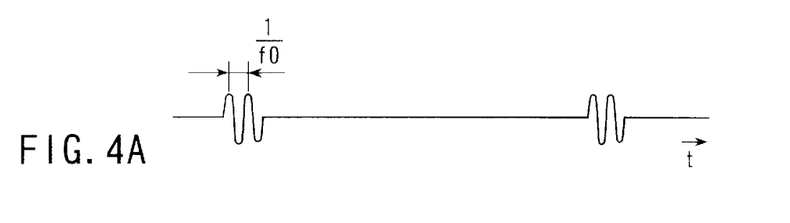
FIG. 4A is a view showing the transmission waveform of an ultrasound pulse in scan operation performed in B-mode alone in this embodiment.
Figure 4B:
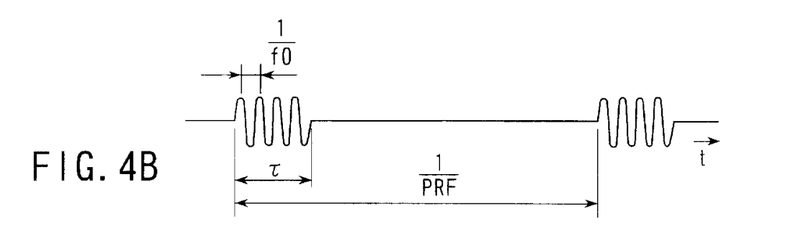
FIG. 4B is a view showing the transmission waveform of an ultrasound pulse in scan operation performed in the power Doppler mode alone in this embodiment.
Figure 4C:
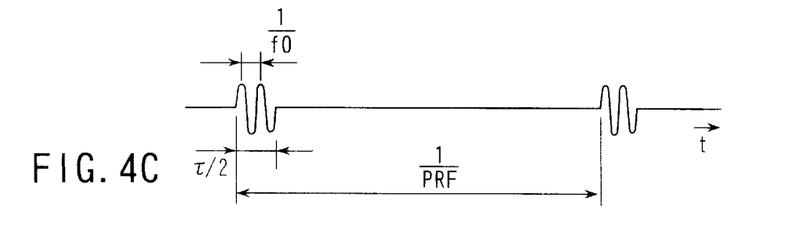
FIG. 4C is a view showing the transmission waveform of an ultrasound pulse in new scan operation performed in the combination of B-mode and the power Doppler mode in this embodiment.

Characteristic features of this embodiment will be described in detail next. FIG. 4A shows the transmission waveform of an ultrasound pulse in a case wherein ultrasound scan operation is performed in B-mode alone. FIG. 4B shows the transmission waveform of an ultrasound pulse in a case wherein ultrasound scan operation is performed in the power Doppler mode alone. In B-mode, the wave number (burst wave number) of a transmission pulse is typically set to 2 (or 1). In this case, letting f0 be the fundamental frequency, the wave train length is given by 2/f0. In the power Doppler mode, the burst wave number is typically set to 4. In this case, the wave train length is given by 4/f0. Note that reference symbol PRF denotes a pulse repeating frequency. FIG. 4C shows the transmission waveform of an ultrasound pulse in a new power Doppler mode serving also as B-mode. In this mode, the wave number (burst wave number) of a transmission pulse transmitted from the transmitting circuit 2 is set to 2 (or 1) as in B-mode.

Figure 5:
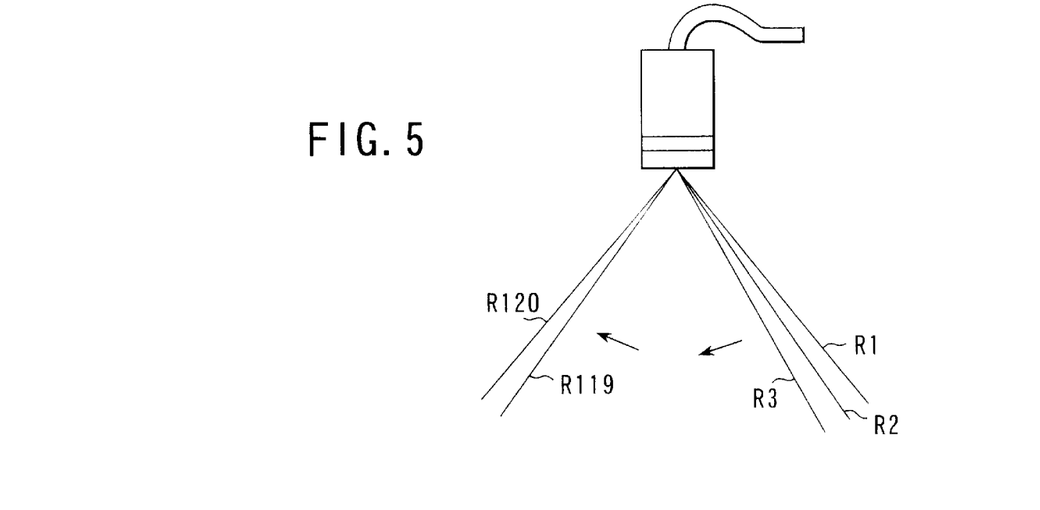
FIG. 5 is a view showing an example of ultrasound scanning lines.
Figure 6:
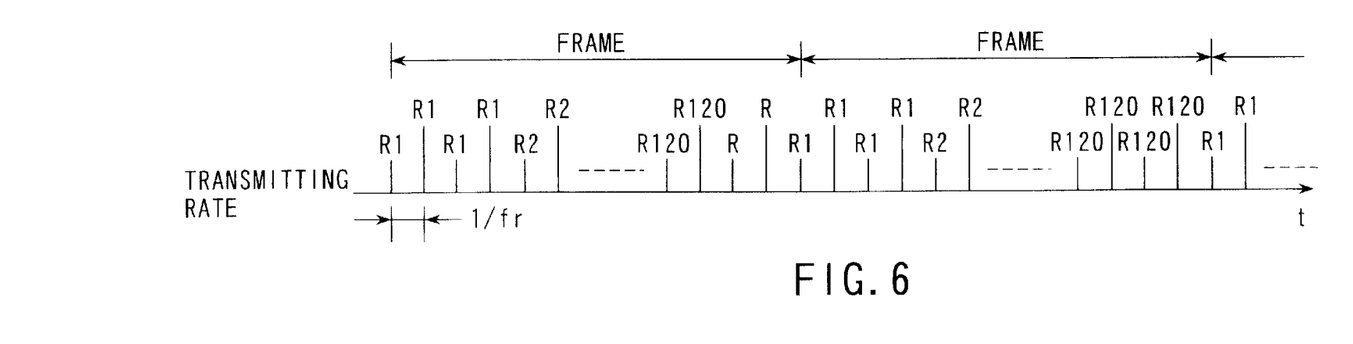
FIG. 6 is a view showing a scan sequence in this embodiment.

As shown in FIGS. 5 and 6, the number of times transmission is repeated in the same direction, i.e., the ensemble size, is set to 4. That is, an ultrasound pulse is repeatedly transmitted four times in each direction. In this sequence, pulse transmission is not performed exclusively for B-mode but is performed for both B-mode and power Doppler. Although four reception signals are available for B-mode display in each direction (scanning line), only one of these signals is used. Alternatively, the four reception signals may be added/averaged before the detecting circuit 4b. This makes it possible to increase the S/N ratio by about 6 dB. The four reception signals in the same direction may be filtered by different echo filters, respectively, and then the resultant signals may be added/averaged after the LOG 4c. With this operation, a B-mode image with reduced speckle can be obtained.

Note that the two amplifiers 13a and 13b are connected to the output stage of the receiving circuit 3 to separately adjust the gains of a B-mode image and power Doppler image. With this arrangement, the respective gains can be adjusted such that the highest gray level of a B-mode tissue image becomes almost equal to that of a power Doppler bloodstream image at the input stage of the image synthesizing unit 7. As described above, the image synthesizing unit 7 selectively outputs a B-mode image from the DSC 6a of the B-mode system or a power Doppler image from the DSC 6b of the power Doppler system which exhibits a higher display gray level. This output is displayed in a gray scale on the display 8. The dummy post processors 10a and 10b for performing gray scale conversion processes respectively suited for a B-mode image and power Doppler image are arranged in the image synthesizing unit 7 to obtain an optimal image after synthesis. As a gray scale conversion curve for a power Doppler image, an S-shaped curve can be suitably used, which suppresses small-amplitude noise and broadens the middle gray scale range so large-amplitude signals regarded as clutter are saturated.

In practicing this scheme, it is preferable that image processing in the frame direction, e.g., persistence be not performed or only weakly performed. This makes it possible to emphasize or maintain a state wherein a bloodstream image is changing with time.

A method of effectively using this embodiment is a method of using an ultrasound contrast medium (contrast echo method). An ultrasound contrast medium improves the sensitivity for a power Doppler image. The bloodstream drawing sensitivity in the scheme of this embodiment is higher than that in B-mode alone. In addition, the spatial resolution of a bloodstream is almost equal to that in B-mode. Since the bloodstream drawing sensitivity improves, the MI (Mechanical Index) value can be decreased as compared with display in B-mode alone, preferably to 0.3 or less. This makes it possible to suppress the collapse of bubbles in the ultrasound contrast medium made of bubbles and prolong the duration of the ultrasound contrast medium.

Further, in the high MI, the bloodstream drawing sensitivity in this embodiment is higher than that in the conventional B-mode harmonic imaging. When the scan is repeated in the high MI condition, most of the contrast medium (micro bubbles) is collapsed. Therefore the medium is not imaged by the conventional B-mode harmonic imaging.

However this embodiment method can sensitively image the remained contrast medium.

The merit of visualization by this invention method is that a bloodstream can be displayed with a high resolution in real time. In the conventional harmonics method or pulse inversion method, since harmonic components originating from a tissue and bloodstream are displayed as identical information, the bloodstream is very difficult to see. According to this invention method of this embodiment, however, since bloodstream image and tissue image data are selected in units of pixels and partly synthesized, the balance of the two images can be easily adjusted. The bloodstream image can be easily emphasized relative to the tissue image, as needed. More specifically, if the gain of B-mode is set to be very lower than the Doppler gain, a bloodstream can be observed with the highest sensitivity. In this invention method of this embodiment, although a power Doppler image contains a clutter image as well as a bloodstream image, since the clutter originates from the tissue, it is smoothly joined to the B-mode image and disappears. In addition, by using the flash echo method in combination with this invention method of this embodiment, perfusion can be visualized with a higher sensitivity.

Conventionally, an intra-tissue bloodstream (perfusion) is observed by intermittently transmitting ultrasound pulses with a high MI value and destroying bubbles. This is because the sensitivity is not high enough to visualize perfusion, and strong ultrasound echoes are obtained by destroying bubbles. By using this scheme, however, perfusion can be visualized by continuous transmission with a low MI value. The operation of this embodiment in the contrast echo mode will be described below.

Figure 7:
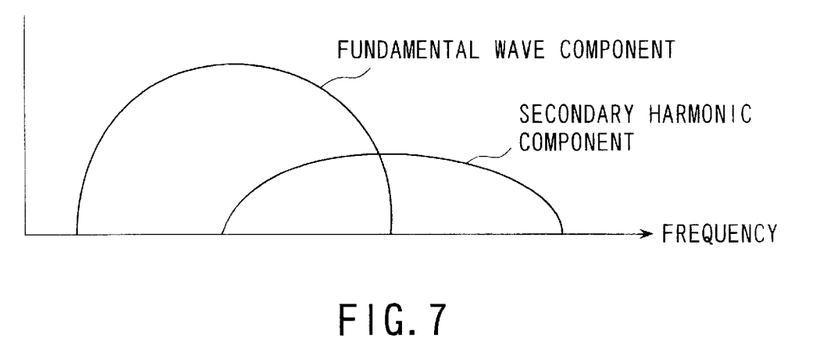
FIG. 7 is a graph showing the frequency characteristics in the distance direction of an output signal from a receiving circuit in FIG. 3.

As shown in FIG. 7, the frequency characteristics of an input signal to the echo filter 4a are mainly comprised of fundamental wave component and a secondary harmonic component generated by reflection and/or nonlinear propagation from an ultrasound contrast medium (microbubble). Only the secondary harmonic component is mainly extracted by the echo filter 4a. In this case, a method of generating a harmonics B-mode image in a filter method is described. However, a pulse inversion method of extracting secondary harmonic components from two pulses with different polarities is also known and can be used here. The signal shown in FIG. 7 is also input to the power Doppler processing unit 5.

Figure 8:
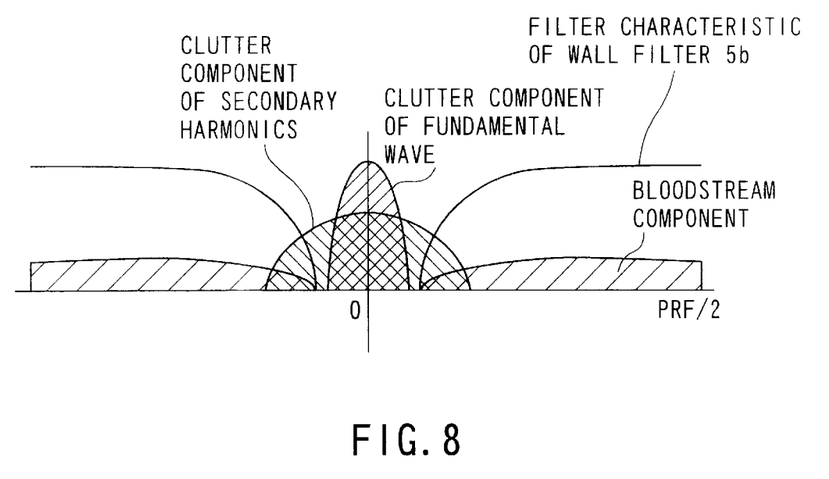
FIG. 8 is a graph showing the Doppler frequency characteristics of an output signal from the receiving circuit in FIG. 3.

FIG. 8 shows Doppler frequency characteristics. Note that since signals in a broadband in the distance direction of 1-wave driving are also input to the power Doppler processing unit 5, the clutter component of a fundamental wave, the clutter component of a secondary harmonics, and a bloodstream component of the fundamental wave or secondary harmonics are distributed as shown in FIG. 8.

In conventional 4- to 8-wave transmission driving, owing to a narrowband, only the Doppler component of a fundamental wave theoretically appears. In this case, the wall filter 5b is provided with filter characteristics that can reduce the clutter component of a fundamental wave to a certain degree. In this case, signals passing through the filter 5b include the leakage clutter of the fundamental wave, part of the clutter of the secondary harmonics, the bloodstream of the fundamental wave, and the bloodstream of the secondary harmonics. In this case, therefore, since the bloodstream component of the fundamental wave also passes through the filter unlike the conventional harmonic power Doppler method in which only the bloodstream component of the secondary harmonics is output, the bloodstream drawing sensitivity improves. Note that the above description is made about the method of performing no pulse inversion. However, the pulse inversion Doppler method is also known, and the same effects as those described above can be obtained even if the above operation is performed by using the pulse inversion Doppler method.

The method of this embodiment makes it possible to draw a cardiac bloodstream, a bloodstream in a thick blood vessel, e.g., a carotid, portal vein, or hepatic vein, or a fast bloodstream without using any ultrasound contrast medium. Such a bloodstream dynamic behavior and tissue image can be displayed with a high resolution.

The functions and effects of this embodiment will be summarized below.

(1) The same transmission condition as in B-mode is set in power Doppler. More specifically, the burst wave number of a transmission pulse for power Doppler, i.e., a burst waveform (pulse string), is set to 1 to 2 as in B-mode, which is smaller than that in the prior art, i.e., 4 to 8. This makes it possible to provide power Doppler with a distance resolution substantially equal to that in B-mode. If, for example, a power Doppler image and B-mode image pass through the wall filter 5b, they have identical information. This phenomenon is closely related to an image synthesizing method (to be described later).

(2) The ensemble size in power Doppler, i.e., the number of times transmission/reception is repeated in the same direction, is set to 2 to 10, preferably 2 to 6, and more preferably 4. The ensemble size in conventional power Doppler is set to 8 to 20, typically 16. If the ensemble size is small, the wall filter 5b cannot sufficiently remove clutter. In this embodiment, since the ensemble size is set to a small value, about 4, clutter cannot be completely removed. However, the clutter originates from a moving tissue, i.e., the power of the clutter represents tissue information as in B-mode. This clutter is joined to a tissue image of a B-mode image portion and can be used as tissue information by partly synthesizing a power Doppler image with a B-mode image. By setting the ensemble size to about 4 in this manner, the frame rate (time resolution) can be increased by two times or more as compared with the conventional power Doppler method.

(3) No transmission/reception dedicated to B-mode is performed, and a reception signal of an ultrasound pulse transmitted for power Doppler is used for the generation of a B-mode image. More specifically, the reception signal obtained by scanning is used for both the generation of a B-mode image and the generation of a power Doppler image. If, therefore, the transmission condition for power Doppler is allowed to be completely the same as that for B-mode, ultrasound waves need not be separately transmitted for B-mode and power Doppler. When scan operation is commonly performed in B-mode and power Doppler, a B-mode image may be generated by using any one of four reception signals (ensemble size: 4) acquired for power Doppler in the same direction. Alternatively, the four reception signals may be added/averaged before detection, and a B-mode image may be generated on the basis of the resultant output. This can increase the S/N ratio. If the reception filter characteristics are changed and these signals are added/averaged after detection, a speckle removing effect can be obtained.

(4) Orthogonal coordinate transformation and processing (dummy post process) equivalent to a post process are performed for a B-mode image and power Doppler image. The gray levels of the pixels of the two images are then compared with each other in units of pixels, and pixels with higher gray levels are selected, thereby partly synthesizing the images. According to this synthesizing method, the problem stemming from synthesis by the conventional threshold method can be solved. The reason for this has been described above.

As described above, the source of clutter in power Doppler is the same as that of a B-mode tissue image. If this component is displayed as a power Doppler image, the image is recognized as clutter (noise). By synthesizing it with a B-mode image, even if the clutter in power Doppler exhibits a higher gray level than the B-mode image and remains after synthesis, this image can be recognized as a tissue image. In the conventional color Doppler and power Doppler methods, the most significant challenge is to remove clutter. In this embodiment, the occurrence of clutter raises no serious problem. In the prior art, clutter is removed together with a slow bloodstream. In this embodiment, since clutter need not be completely removed, an improvement in slow bloodstream sensitivity can also be achieved.

(Modification)

According to the above description, transmission pulses are commonly used for B-mode and power Doppler. However, to satisfy both requirements for a high resolution in B-mode and a high sensitivity in power Doppler, different transmission pulses may be used for the respective modes. For example, 1-wave driving is used for B-mode, and 2-wave driving is used for power Doppler.

In the image synthesizing method described above, pixels of a B-mode image and power Doppler image which exhibit higher gray levels are selectively output in units of pixels. However, a method of adding pixels is also available. It is important for an image synthesizing method not to separately perform processing for a B-mode image and power Doppler image.

In addition, according to the above description, a B-mode image and power Doppler image are added after coordinate transformation. However, these images may be synthesized before coordinate transformation according to the same synthesis logic as described above, and coordinate transformation may be performed afterward. This makes it possible to reduce the circuit size associated with a display system.

As has been described above, according to the present invention, the distance resolution can be improved by decreasing the burst wave number to the same or nearly same value as for a B-mode image. In addition, the time resolution can be improved by decreasing the ensemble size, i.e., the number of times an ultrasound pulse is transmitted/received in the same direction. When the distance resolution and time resolution improve in this manner, clutter increases. However, by partly synthesizing the B-mode image and power Doppler image according to the gray levels, clutter which is essentially a tissue echo can be buried in a B-mode tissue image and effectively used as useful information representing a tissue structure, thereby substantially solving the problem stemming from the clutter as noise. When a bloodstream is synthesized with clutter (tissue), it may be difficult to identify them. However, since the bloodstream is faster than the clutter, and the time resolution improves, the flicker effect (flicker) is enhanced. This makes it possible to satisfactorily discriminate clutter with enhanced flicker from clutter with less flicker.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnosis apparatus comprising:
an ultrasound probe;
a beam-former configured to scan an object to be examined with ultrasound waves through said ultrasound probe;
a B-mode processor configured to generate B-mode data on the basis of a reception signal output from said beam-former;
a power Doppler processor configured to generate power Doppler data on the basis of the reception signal output from said beam-former, the power Doppler data being generated on the basis of the reception signal acquired under transmission conditions that a burst wave number is equal or substantially equal to that for the B-mode data, and an ensemble number is set to one of 2 to 10; and
a synthesizer configured to generate 1-frame synthetic image data by synthesizing the B-mode data with the power Doppler data.

2. An apparatus according to claim 1, wherein the ensemble size is one of 2 to 6.

3. An apparatus according to claim 2, wherein the ensemble size is 4.

4. An apparatus according to claim 1, wherein the burst wave number is 1 or 2.

5. An apparatus according to claim 1, further comprising a post processor configured to perform post process for the synthetic image.

6. An apparatus according to claim 1, wherein said synthesizer comprises a dummy post process circuit configured to perform a dummy post process equivalent or substantially equivalent to a post process performed by said post processor for the B-mode data and power Doppler data, a comparing circuit configured to compare pixel values of the B-mode image data with pixel values of the power Doppler data pixel by pixel, and a selecting circuit configured to select higher pixel values of the pixel values of the B-mode data and power Doppler data pixel by pixel of pixel on the basis of outputs from said comparing circuit.

7. An apparatus according to claim 6, wherein said dummy post process circuit comprises two dummy post processor to parallelly execute a dummy post process for the B-mode data and a dummy post process for the power Doppler data.

8. An apparatus according to claim 6, further comprising a controller for controlling a processing condition in said dummy post process circuit in accordance with a process condition in said post processor.

9. An apparatus according to claim 1, wherein said synthesizer compares display gray levels of the B-mode data with display gray levels of the power Doppler pixel by pixel, and selects pixel values exhibiting higher gray levels.

10. An apparatus according to claim 1, further comprising first and second amplifiers respectively connected to input stages of said B-mode processor and power Doppler processor to separately set a gain for an input signal to said B-mode processor and a gain for an input signal to said power Doppler processor.

11. An apparatus according to claim 1, further comprising a converter configured to convert a highest gray level of the B-mode data and a highest gray level of the power Doppler data to substantially the same level.

12. An apparatus according to claim 1, wherein the B-mode data and power Doppler data are generated from the same reception signal.

13. An apparatus according to claim 1, wherein scan operation for the B-mode data is commonly performed for the power Doppler data.

14. An apparatus according to claim 1, wherein scan operation for the B-mode data is performed independently of scan operation for the power Doppler data.

15. An apparatus according to claim 1, wherein the power Doppler data is generated on the basis of a plurality of reception signals corresponding to a plurality of ultrasound pulses repeatedly transmitted in the same direction with an ensemble size set to one of 2 to 10, and the B-mode data is generated on the basis of the plurality of reception signals.

16. An apparatus according to claim 1, wherein the power Doppler data is generated on the basis of a plurality of reception signals corresponding to a plurality of ultrasound pulses repeatedly transmitted in the same direction with an ensemble size set to one of 2 to 10, and the B-mode data is generated on the basis of a sum signal of the plurality of reception signals.

17. An apparatus according to claim 1, further comprising a display for displaying the synthetic image in a gray scale.

18. An ultrasound diagnosis apparatus comprising:

an ultrasound probe;

a beam-former configured to transmit/receive an ultrasound wave to/from an object to be examined through said ultrasound probe under conditions that a burst wave number is 1 or 2, and an ensemble size is one of 2 to 10;

a processor configured to parallelly generate B-mode data and power Doppler data on the basis of a reception signal output from said beam-former; and a synthesizer configured to generate 1-frame synthetic image data by partly synthesizing the B-mode data with the power Doppler data.

19. An ultrasound diagnosis apparatus comprising:

an ultrasound probe;

a beam-former configured to transmit/receive an ultrasound wave to an object to be examined through said ultrasound probe;

a B-mode processor configured to generate B-mode data on the basis of a reception signal output from said beam-former;

a power Doppler processor configured to generate power Doppler data on the basis of a reception signal output from said beam-former; and a synthesizer configured to generate 1-frame synthetic image data by partly synthesizing the B-mode data with the power Doppler data, a comparing circuit to compare pixel values of the B-mode data with pixel values of the power Doppler image data pixel by pixel, and a selecting circuit configured to select higher pixel values of the pixel values of the B-mode data and power Doppler data pixel by pixel on the basis of outputs from said comparing circuit.

* * * * *